(12) United States Patent
Geist et al.

(10) Patent No.: US 8,439,952 B2
(45) Date of Patent: May 14, 2013

(54) CONNECTING ROD FOR BONE ANCHORS HAVING A BIORESORBABLE TIP

(75) Inventors: Wyatt Drake Geist, Davie, FL (US); Christopher Walsh, Parkland, FL (US)

(73) Assignee: Integrity Intellect, Inc., Jupiter, FL (US)

( * ) Notice: Subject to any disclaimer, the term of this patent is extended or adjusted under 35 U.S.C. 154(b) by 378 days.

(21) Appl. No.: 11/462,566

(22) Filed: Aug. 4, 2006

(65) Prior Publication Data
US 2008/0051781 A1 Feb. 28, 2008

(51) Int. Cl.
*A61B 17/70* (2006.01)

(52) U.S. Cl.
USPC ............... 606/259; 606/261; 606/76; 606/77

(58) Field of Classification Search .............. 606/259, 606/264, 278, 76, 77, 261
See application file for complete search history.

(56) References Cited

U.S. PATENT DOCUMENTS

| 4,369,769 | A | | 1/1983 | Edwards |
| 5,525,646 | A | * | 6/1996 | Lundgren et al. ............ 523/105 |
| 5,810,821 | A | * | 9/1998 | Vandewalle .................... 606/65 |
| 5,836,949 | A | * | 11/1998 | Campbell et al. ............... 606/62 |
| 6,102,912 | A | * | 8/2000 | Cazin et al. ................... 606/86 A |
| 6,331,312 | B1 | * | 12/2001 | Lee et al. ....................... 424/426 |
| 6,530,929 | B1 | | 3/2003 | Justis et al. |
| 6,623,484 | B2 | | 9/2003 | Betz et al. |
| 7,008,422 | B2 | | 3/2006 | Foley et al. |
| 2001/0039450 | A1 | * | 11/2001 | Pavcnik et al. ............. 623/1.24 |
| 2002/0161368 | A1 | * | 10/2002 | Foley et al. .................... 606/61 |
| 2002/0169465 | A1 | * | 11/2002 | Bowman et al. ............. 606/151 |
| 2005/0038432 | A1 | * | 2/2005 | Shaolian et al. ............... 606/61 |
| 2005/0079088 | A1 | * | 4/2005 | Wirth et al. ................... 420/402 |
| 2005/0171540 | A1 | | 8/2005 | Lim et al. |
| 2006/0041259 | A1 | | 2/2006 | Paul et al. |
| 2007/0032794 | A1 | | 2/2007 | Weber et al. |
| 2007/0167091 | A1 | | 7/2007 | Schumacher |

* cited by examiner

*Primary Examiner* — Eduardo C Robert
*Assistant Examiner* — Julianna N Harvey
(74) *Attorney, Agent, or Firm* — McHale & Slavin, P.A.

(57) ABSTRACT

The invention provides a connecting rod for bone anchors such as pedicle screws. The rod is constructed to include a main shaft portion that is not bioresorbable and a tip portion that is bioresorbable. The tip facilitates percutaneous insertion into a patient's body. After placement of the rod, the bioresorbable tip is resorbed preventing post-operative complications such as impingement of adjacent spinal facet joints.

8 Claims, 6 Drawing Sheets

FIG. 5

CONNECTING ROD FOR BONE ANCHORS HAVING A BIORESORBABLE TIP

FIELD OF THE INVENTION

The invention generally relates to surgical implants; particularly to devices for fixation of bony structures and most particularly to a connecting rod for bone anchors suitable for percutaneous insertion and constructed to include a main shaft portion that is not bioresorbable and a tip portion that is bioresorbable.

BACKGROUND OF THE INVENTION

Healing and/or structural correction is greatly facilitated when a bone is fixed, i.e. stabilized, in the proper position. Various devices and techniques for stabilization of bone are well known and routinely practiced in the medical arts. Long bones have been stabilized using such devices as plates, slings, external casts, splints, screws and braces. The spine has been stabilized using rod and fastener systems. For example, fasteners such as screws, clamps, hooks, claws or bolts are placed into each vertebra and connected by a rod attached to the fasteners. Tension or compression force is applied to the rod between each consecutive fastener for fixation of the vertebrae. Such a system can be used on a single vertebra and/or on multiple vertebrae.

Bone screws are commonly used as fasteners for alignment and fixation of vertebral bodies. These screws are inserted into the spinal pedicle, the bony process projecting backward from the vertebral body, and stabilized with connecting rods placed longitudinally with regard to the vertebrae. Although surgical insertion of pedicle screws has successfully treated non-unions, instability, injuries and disease of the spine, it is not without disadvantages.

A serious post-operative complication after insertion of pedicle screws is impingement of the movement of facet joints. Facet joints link the vertebrae together and their hinge-like movement enables flexion (bending forward) and extension (bending backward) of the spine. When pedicle screws are connected the connecting elements are placed within an area that is normally an empty space. This infringement of space limits the range of motion of the facet joints. Additionally, if the pedicle screws are inserted percutaneously using a minimally invasive device, the tip which facilitates the insertion, but performs no other function, remains attached to the connecting rod further impinging space. A patient with impinged facet joints can suffer difficult and limited movement along with extreme discomfort and pain. The primary purpose of the surgical placement of pedicle screws is to improve and/or correct symptoms of back problems, thus these side effects are unacceptable.

Accordingly, a need exists in the surgical arts for connecting elements that are compatible with minimally invasive techniques and capable of providing effective stabilization, but are less bulky and less disruptive of normal vertebral functioning than the currently available connecting elements.

PRIOR ART

Researchers have attempted to circumvent some of the disadvantages associated with conventional surgical implants by using implants constructed from bioresorbable materials. Most bioresorbable materials are polymers that are slowly hydrolyzed into lactic acid which is then metabolized by the liver into carbon dioxide and water and easily eliminated by the body. Bioresorbable implants have many advantages, such as, versatility (they can be designed for many types of tissue), predictability (with regard to absorption rates) and strength (during bone healing and/or correction). Bioresorbable implants do not obscure imaging results (on X-ray, MRI, CT scan), do not require additional surgery for removal and reduce the risk of implant failure, such as impingement of spinal facet joints. Furthermore, the use of bioresorbable implants may reduce immune reactions and osteolysis of the healing bone that can result with the use of conventional, non-bioresorbable implants.

Bone tissue responds well in regions of stress and/or pressure. For example, when stress is reduced or removed by insertion of an implant, the implant bears the entire weight load for the bone as long as it remains inserted. Thus, the bone may not heal properly as the implant is providing the structure that the healed bone should be providing. Bioresorbable implants are ideal in that they avoid this problem by encouraging repair since they resorb as tissue is healing and the tissue gradually lessons dependency on the implant for support.

U.S. Pat. No. 4,369,769, issued to Charles C. Edwards on Jan. 25, 1983, discloses a spinal fixation device in which sleeves or spacers are placed around or over spinal rods to provide an appropriate fit between the rod and the spine in order to achieve greater pressure and thus greater correction of spinal deformities. These sleeves or spacers are disclosed as having variable thicknesses and are constructed from any biologically compatible material, including bioresorbable materials.

U.S. Pat. No. 6,623,484 B2, issued to Betz et al. on Sep. 23, 2003 discloses a method for treatment and correction of spinal deformities without the need for fusion of the intervertebral disk space. A surgical technique is disclosed in which opening and closing osteotomies are created in the affected vertebrae. Correction devices are provided which hold the osteotomies in either the closed or open orientations. These correction devices also include connection members which can be used to engage the devices to an elongated member, such as a spinal rod. Once bone union has occurred in the treated vertebrae, the spinal rod can be disconnected from the correction devices and removed from the patient. In one embodiment, the spinal rods are formed of a bioresorbable material to eliminate the need for a second surgery to remove the rod from the patient's body.

US Patent Application Publication 2005/0171540 A1, Lim et al., published on Aug. 4, 2005, discloses instruments and methods for minimally invasive spinal stabilization. The disclosed instrument introduces a flexible stabilization element into a patient and secures it to one or more anchors, for example, bone screws. Lim et al. also disclose many embodiments using connecting rods for the anchors (bone screws). One such connecting rod, shown in FIG. 38 of the Lim application, includes two distal end portions and a center portion connecting the distal portions. The distal end portions are constructed of a non-bioresorbable metal material and the center connecting portion is constructed of a bioresorbable material. The bioresorbable material is resorbed to release the connection between two adjacent anchors.

SUMMARY OF THE INVENTION

The surgical arts have advanced to the point that minimally invasive techniques for percutaneous placement of surgical implants and instruments are commonly practiced. Compared to the requirements of conventional "open surgery", the amount and size of incisions is decreased with the use of minimally invasive techniques. Decreased invasiveness has led to reduced trauma/post-operative pain with reduction of length of hospital stay and recovery time for the patient. In addition to individual benefits, health care as a whole is benefitted by both reduced costs and burden on the system.

Many surgical instruments have been adapted for use with percutaneous techniques. For example, a trocar provides access to the desired site within a body cavity during a minimally invasive surgical procedure. The obturator, i.e. piercing end, of the trocar penetrates the tissue and is shaped to enlarge the opening created as the trocar is advanced.

Bone anchors have been percutaneously placed and connected. Connecting elements have been adapted for such purpose by attaching a trocar-type tip to the distal end of a rod. However, although the tip facilitates the insertion, it performs no other function and remains attached to the connecting rod after placement impinging space and thus movement of the facet joints. A need remains for connecting elements which do not interfere with normal functioning.

In order to meet the need in the surgical arts, the instant invention provides connecting elements that are capable of providing effective stabilization while minimizing disruption of normal vertebral functioning. These connecting elements can be percutaneously inserted and are compatible for application with minimally invasive surgical techniques. Although a rod is exemplified herein, other such connecting elements known to one skilled in the art are also contemplated.

The connecting rod of the invention is comprised of two portions, a main shaft portion constructed of a non-bioresorbable material and a tip portion constructed of a bioresorbable material. The non-bioresorbable material of the shaft can be, but is not limited to, a metal, such as titanium, stainless steel, or cobalt-chrome alloys or the shaft portion can be porcelain and/or mixtures of all of these materials. The term "bioresorbable material" is intended to encompass any non-toxic, non-immunogenic material, natural or synthetic, capable of being formed into a tip which after insertion is gradually hydrolyzed and absorbed over a finite period of time by chemical/biological activity in the body. Illustrative, albeit non-limiting, examples are polylactic acid, polyglycolic acid, polycaprolactone, polyanhydrides, polydioxanone, polyamino acids, trimethylene carbonate, 1,5-dioxepan-2-one, copolymers of lactic acid, hydroxyapatite and alginates. The tips of the instant invention can also be made out of bioresorable metals such as magnesium alloys and zinc alloys as described in U.S. Pat. No. 6,854,172 B2 (Kaese et al.) or made out of blends of bioresorbable polymers as described in U.S. Pat. No. 6,583,232 B1 (Brown). Commercially available bioresorbable materials such as LACTOSORB (Walter Lorenz Surgical, Inc. Jacksonville, Fla.) can also be used to construct the tips of the instant invention.

Although the described connecting rod is exemplified for use with vertebral pedicle screws, it is contemplated for use in any bone stabilization procedure where the implant can cause disruption of normal functioning of the affected bone and surrounding tissues.

It is an objective of the instant invention to provide connecting elements for bone anchors that are compatible with minimally invasive techniques and capable of providing effective stabilization, but are less bulky and less disruptive of normal vertebral functioning than the currently available connecting elements.

It is an objective of the instant invention to provide a connecting rod for bone anchors comprising at least one bioresorbable part.

It is another objective of the instant invention to provide a rod for connecting bone anchors comprising; a shaft portion constructed of a non-bioresorbable material and at least one tip portion constructed of a bioresorbable material.

It is yet another objective of the instant invention to provide a rod for connecting pedicle screws comprising two portions; a shaft portion constructed of a non-bioresorbable material and a trocar tip constructed of a bioresorbable material.

Other objectives and advantages of the instant invention will become apparent from the following description taken in conjunction with the accompanying drawings wherein are set forth, by way of illustration and example, certain embodiments of the instant invention. The drawings constitute a part of this specification and include exemplary embodiments of the present invention and illustrate various objects and features thereof.

DETAILED DESCRIPTION OF THE INVENTION

For the purposes of promoting an understanding of the principles of the invention, reference will now be made to the embodiments illustrated in the drawings and specific language will be used to describe the same. However, the illustrated embodiments are merely exemplary. It is understood that no limitation of the scope of the invention is thereby intended. Any alterations and further modifications in the illustrated devices, and such further application of the principles of the invention as illustrated herein are contemplated as would normally occur to one skilled in the art to which the invention relates.

Generally, the invention provides a connecting rod for bony stabilization devices (also referred to herein as anchors or fasteners) and is compatible for use with minimally invasive surgical techniques. This connecting rod is constructed to include at least two portions; a main shaft portion that is not bioresorbable and a tip portion that is bioresorbable. After placement of the rod, the bioresorbable tip is resorbed into the patient's body for reduction of post-operative complications such as impingement of adjacent spinal facet joints.

Joint impingement is a serious side effect of surgical installation of bone anchors such as pedicle screws. The discomfort felt by the patient may be worse than the discomfort of the original condition being treated. Thus, it is very important that these stabilization devices do not further disrupt the function of the tissues that they are meant to treat.

Figure 1A:
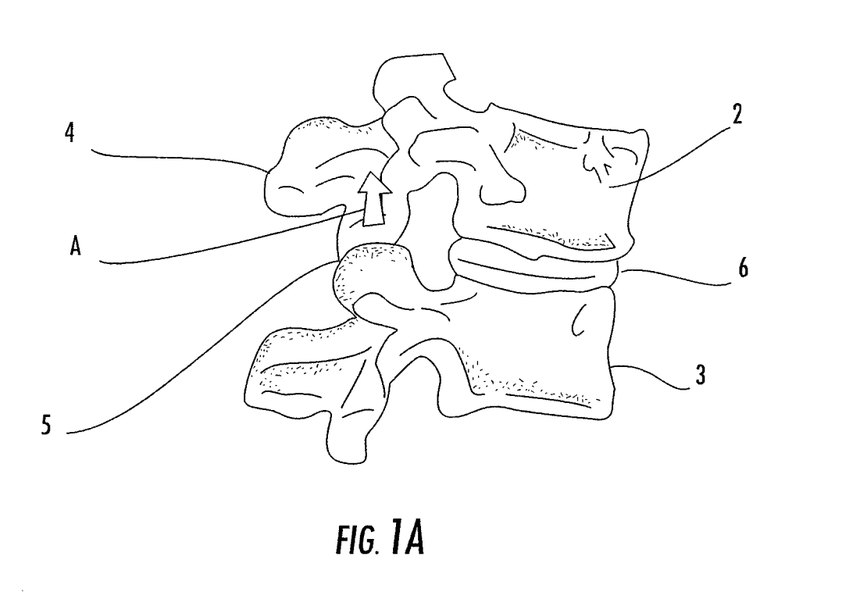
FIGS. 1A-B show a side perspective view of vertebral flexion (FIG. 1A) and extension (FIG. 1B).
Figure 1B:
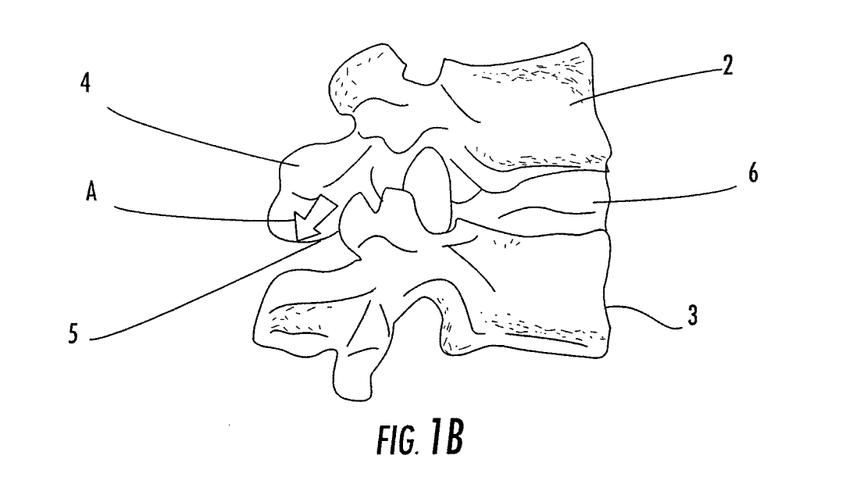

For purposes of explanation, illustration of the movement of the facet joints is provided in FIGS. 1A-B.

FIG. 1A illustrates spinal flexion, i.e. forward movement of a pair of vertebral bodies 1. Facet joints 5 connect upper (superior) vertebral body 2 and lower (inferior) vertebral body 3. Forward movement lifts pedicle 4 upward; direction shown by bolded arrow A. The intervertebral disc 6 is shown between vertebral bodies 2 and 3.

FIG. 1B illustrates spinal extension, i.e. backward movement of the pair of vertebral bodies 1. Facet joints 5 connect upper (superior) vertebral body 2 and lower (inferior) vertebral body 3. Backward movement depresses pedicle 4; direction shown by bolded arrow A. The intervertebral disc 6 is shown between vertebral bodies 2 and 3.

Figure 2:
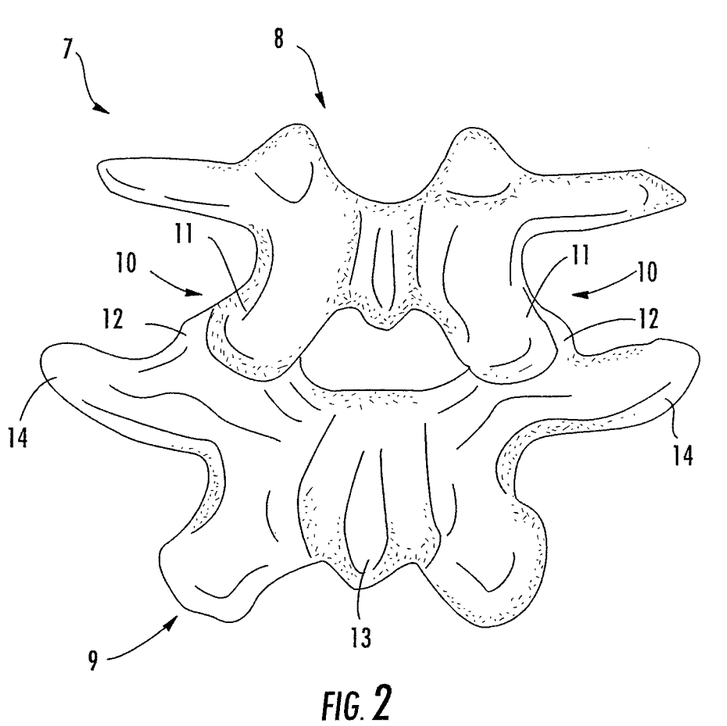
FIG. 2 is a posterior view of a pair of lumbar vertebrae.

For purposes of explanation, FIG. 2 shows a posterior view of a pair of lumbar vertebrae. Although lumbar vertebrae are illustrated, the invention can be used with any adjacent vertebrae. The pair of vertebrae 7 is comprises of superior (upper) vertebra 8 and inferior (lower) vertebra 9. The facet joints 10 between the pair 7 are comprised of inferior facet 11 of superior vertebra 8, and superior facet 12 of inferior vertebra 9. The spinous process 13 and the transverse processes 14 are also shown.

Figure 3:
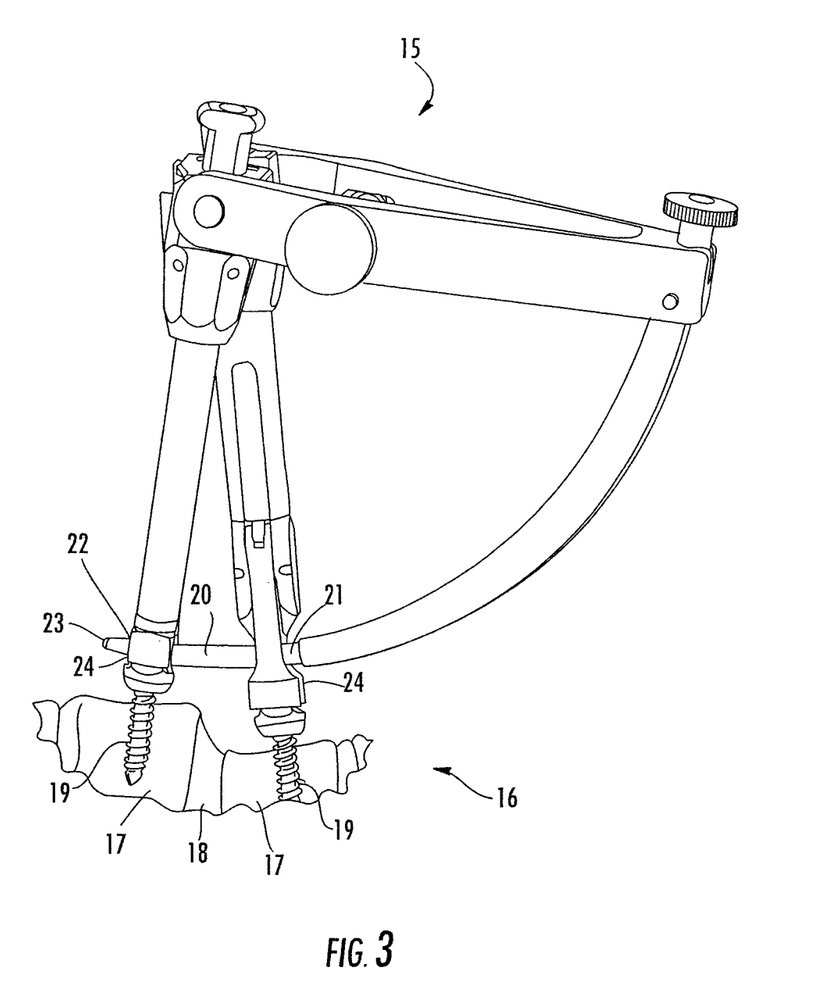
FIG. 3 is an elevation view of an installation instrument for inserting a connecting rod between two pedicle screws in adjacent vertebrae, and forming the spinal fixation assembly of the present invention.

In the illustrated embodiment of the invention, connecting rods are percutaneously inserted into pedicle screws in a minimally invasive surgical approach using an instrument 15 as shown in FIG. 3. For purposes of reference a vertebral segment 16 is shown comprising adjacent vertebral bodies 17 separated by disc space 18. Connecting rod 24 includes a shaft 20 having a length between a connecting end 21 and an insertion end 22 sufficient to connect at least two bone anchors 19. The length of shaft 20 is selected to compatible with the method of insertion as percutaneous insertion requires a longer rod. Shaft 20 as shown is an elongated rod curved along its length between ends 21 and 22 with a radius of curvature R. However, it should be understood that shaft 20 can include any known configuration. Tip 23 coupled to insertion end 22 forms a path through the tissue to facilitate installation of shaft 20 into passageways of anchors engaged to bony structures to stabilize, i.e. fix, the bony structure. The tip 23 is constructed of bioresorbable material and, after a period of time, is resorbed into the body. After resorption of the tip 23, the non-bioresorbable shaft 20 remains, connecting bone anchors 19 between adjacent vertebrae without inhibiting movement.

Figure 4A:
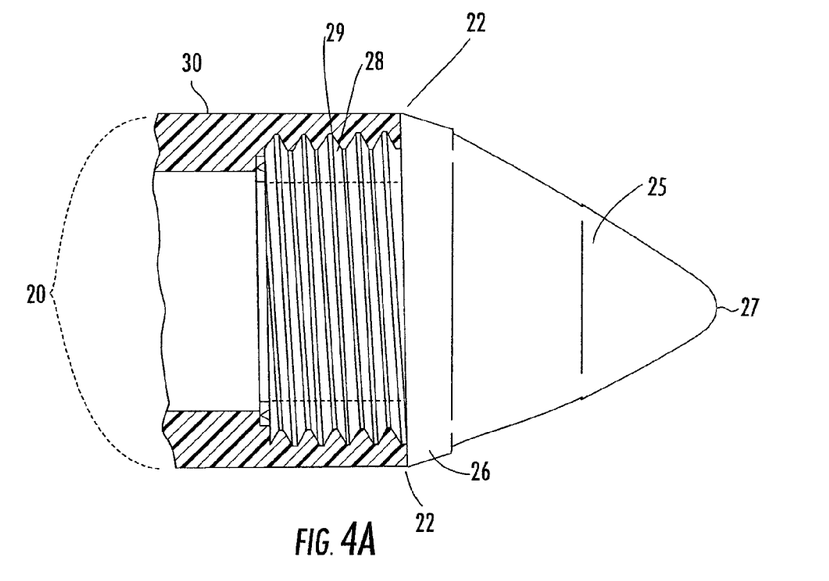
FIG. 4A is a side elevation view of the tip coupled via engaged helical threads with an interior sectional view of the shaft.
Figure 4B:
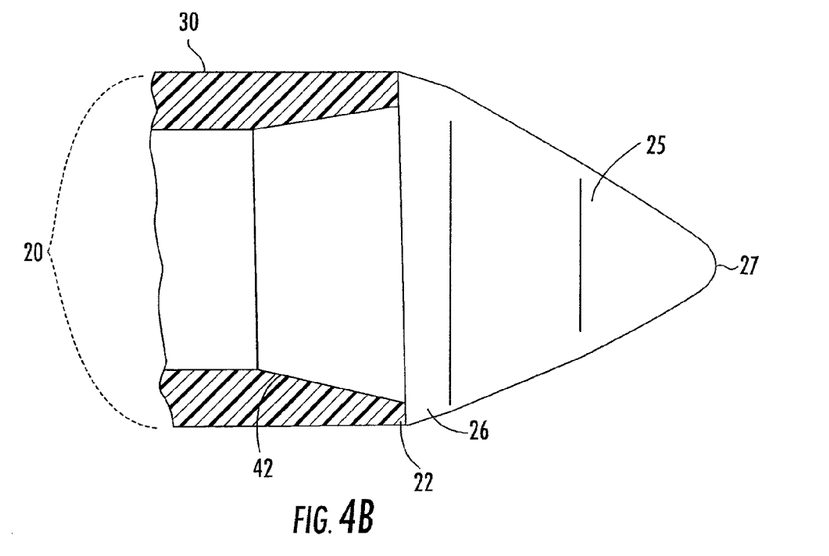
FIG. 4B is a side elevation view of the tip coupled via engaged locking tapers with an interior sectional view of the shaft.
Figure 4C:
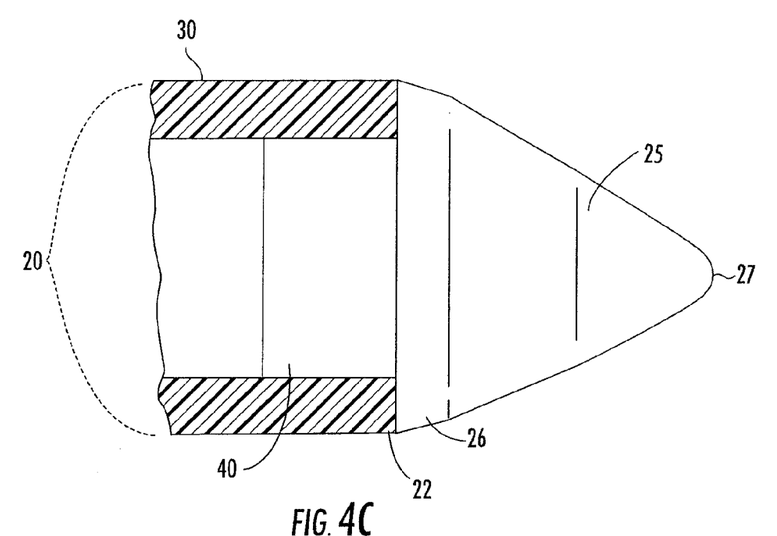
FIG. 4C is a side elevation view of the tip coupled via engaged interference fit with an interior sectional view of the shaft.
Figure 4D:
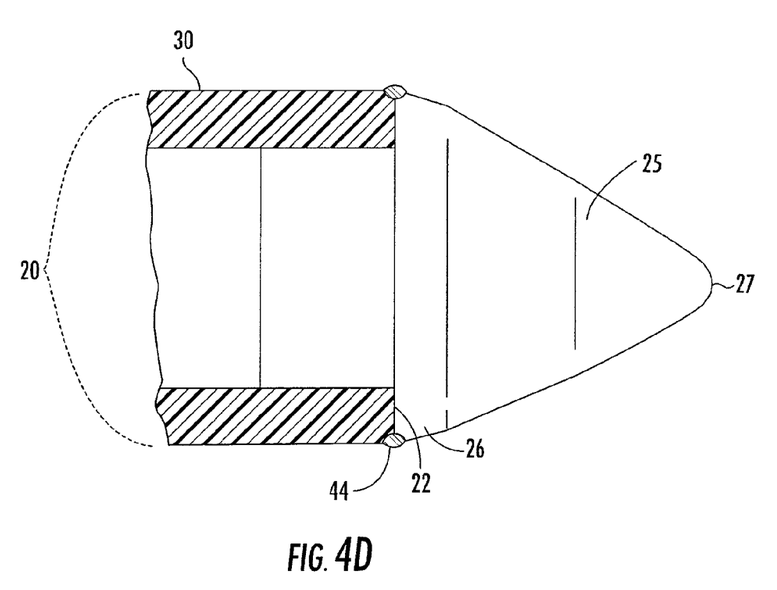
FIG. 4D is a side elevation view of the tip coupled via laser weld with an interior sectional view of the shaft.

An embodiment for coupling the bioresorbable tip to the non-bioresorbable shaft is illustrated in FIGS. 4A-D. A mating threaded attachment 29 is provided between the annulus 28 descending from the tip base 26 and the insertion end 22 of the shaft 20. The annulus portion 28 of the trocar-type tip 25 is threaded 29 and the insertion end 22 of the shaft 20 has mating threads 30 to receive the threads 29 on annulus 28. (see FIG. 4A) Although threads are the exemplified embodiment, other methods for coupling the bioresorbable tip to the non-bioresorbable shaft known to those of skill in the art are contemplated, such as, but not limited to, press fits 40 (FIG. 4C), locking buttons, locking tapers 42 (FIG. 4B) and laser welding 44 (FIG. 4D).

Figure 5:
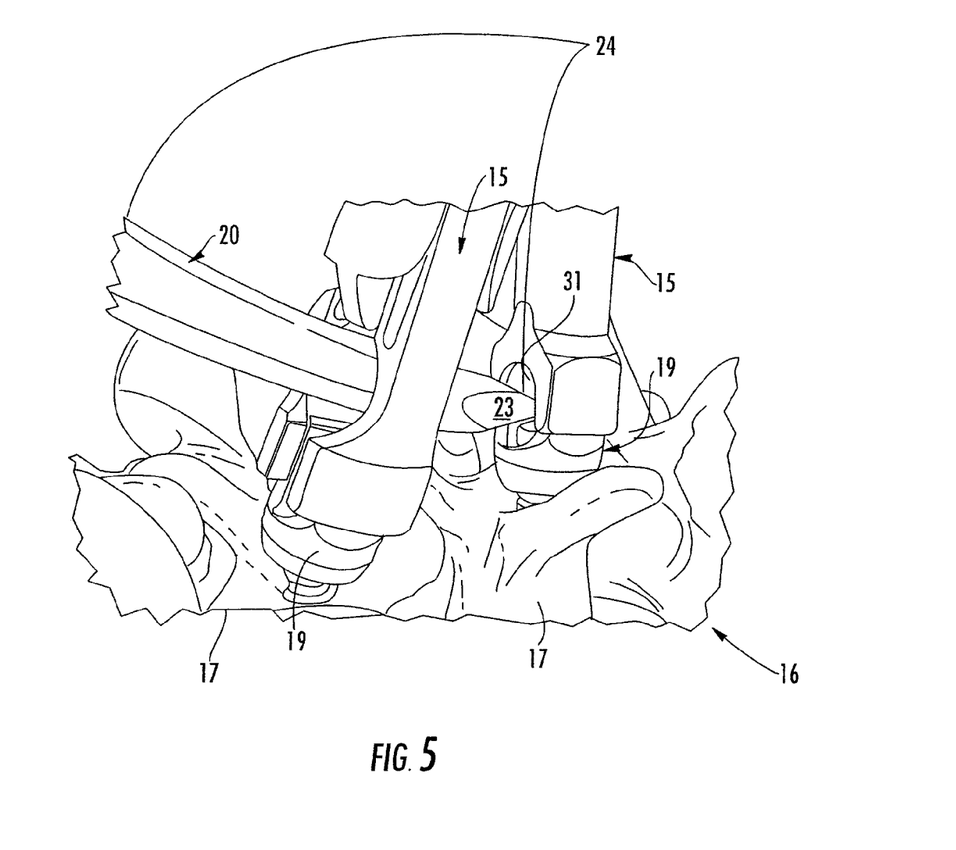
FIG. 5 is a perspective view of a vertebral pair and anchors with the connecting rod positioned for insertion into the passageway through the anchors.

FIG. 5 shows the percutaneous insertion of connecting rod 24 in vertebral segment 16. Anchors 19 are shown installed in adjacent vertebral bodies 17. Instrument 15 guides and positions connecting rod 24 through passage 31 between bone anchors 19.

Although the described connecting rod is exemplified for use with vertebral pedicle screws, it is contemplated for use in any percutaneous surgical procedure wherein the cutting tip provides no function other than creating a passageway.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An improved connecting rod for use on an animal subject, said connecting rod used in conjunction with an installation instrument having anchor extensions coupled to at least two bone anchors, a portion of the instrument moveable through an arcing trajectory with respect to said bone anchors to position said connecting rod to a position proximate said at least two bone anchors, the improvement comprising:

a connecting rod, said connecting rod including a main shaft portion and a tip portion, said main shaft portion constructed of a single piece of material being sufficiently rigid to be pushed through soft animal tissue when grasped at a first distal end, said main shaft having a longitudinal centerline that is arced to substantially match said arcing trajectory and a length sufficient to connect said at least two bone anchors, a second distal end of said main shaft having an aperture therein, said aperture extending generally along said centerline and sized to accept a portion of said tip to retain said tip in alignment with said arcing longitudinal centerline, said tip being constructed from a bioresorbable material, said tip having a base end and an insertion end, said insertion end of said tip being constructed and arranged for forming a path through animal tissue to facilitate installation of said main shaft into said at least two bone anchors, said tip base including a projection sized and shaped to enter said aperture, said projection having a side surface constructed and arranged to cooperate with said aperture for securing said tip to said main shaft, said connecting rod having a first overall length causing impingement with an adjacent bony structure, said connecting rod having a second length after a predetermined time to eliminate said impingement with said adjacent bony structure.

2. The improved connecting rod for use on an animal subject of claim 1 wherein said bone anchors are pedicle screws.

3. The improved connecting rod for use on an animal subject of claim 1 wherein said insertion end of said tip includes a trocar shape.

4. The improved connecting rod for use on an animal subject of claim 1 wherein said base end of said tip and said aperture of said main shaft include mating helical threads.

5. The improved connecting rod for use on an animal subject of claim 1 wherein said base end of said tip and said aperture of said main shaft include mating locking tapers.

6. The improved connecting rod for use on an animal subject of claim 1 wherein said base end of said tip and said aperture of said main shaft include an interference fit.

7. The improved connecting rod for use on an animal subject of claim 1 wherein said base end of said tip and said aperture of said main shaft include a laser weld for securing said tip and said main shaft together.

8. The improved connecting rod for use on an animal subject of claim 1 wherein said bioresorbable material is selected from the group consisting of polylactic acid, polyglycolic acid, polycaprolactone, polyanhydrides, polydioxanone, polyamino acids, trimethylene carbonate, 1,5-dioxepan-2-one, copolymers of lactic acid, hydroxyapatite, alginates and bioresorbable metals.

* * * * *